United States Patent
Nogoshi et al.

(10) Patent No.: US 10,465,364 B2
(45) Date of Patent: Nov. 5, 2019

(54) WATER DISCHARGE APPARATUS

(71) Applicant: TOTO LTD., Kitakyushu-shi, Fukuoka (JP)

(72) Inventors: Yusuke Nogoshi, Kitakyushu (JP); Masahiro Kuroishi, Kitakyushu (JP); Takamasa Suzuki, Kitakyushu (JP); Kenta Suzuki, Kitakyushu (JP); Yusuke Nakamura, Kitakyushu (JP); Koki Nagano, Kitakyushu (JP)

(73) Assignee: TOTO LTD., Fukuoka (JP)

( * ) Notice: Subject to any disclaimer, the term of this patent is extended or adjusted under 35 U.S.C. 154(b) by 338 days.

(21) Appl. No.: 15/522,482

(22) PCT Filed: Sep. 9, 2015

(86) PCT No.: PCT/JP2015/075549
§ 371 (c)(1),
(2) Date: Apr. 27, 2017

(87) PCT Pub. No.: WO2016/072148
PCT Pub. Date: May 12, 2016

(65) Prior Publication Data
US 2017/0314242 A1    Nov. 2, 2017

(30) Foreign Application Priority Data
Nov. 6, 2014 (JP) ................. 2014-226311

(51) Int. Cl.
| | | |
|---|---|---|
| *B08B 3/00* | (2006.01) | |
| *E03C 1/04* | (2006.01) | |
| *A61L 2/18* | (2006.01) | |
| *C25B 9/06* | (2006.01) | |
| *C25B 15/02* | (2006.01) | |
| *C25B 15/08* | (2006.01) | |
| *E03C 1/14* | (2006.01) | |

(52) U.S. Cl.
CPC .............. *E03C 1/0405* (2013.01); *A61L 2/18* (2013.01); *C25B 9/06* (2013.01); *C25B 15/02* (2013.01); *C25B 15/08* (2013.01); *E03C 1/14* (2013.01); *A61L 2202/11* (2013.01); *A61L 2202/14* (2013.01)

(58) Field of Classification Search
CPC .......... A61L 2/0088; A61L 2/183; A61L 2/18; A61L 2202/15; E03C 1/0405; C25B 15/08
USPC .......... 422/292; 134/94.1, 172, 198; 204/193
See application file for complete search history.

(56) References Cited

FOREIGN PATENT DOCUMENTS

| | | | | |
|---|---|---|---|---|
| JP | H10-82083 A | | 3/1998 | |
| JP | 2010-090586 | * | 4/2010 | ............ E03C 1/046 |
| JP | 2010-090586 A | | 4/2010 | |

OTHER PUBLICATIONS

The Japan Patent Office English Translation of the Detailed Description section of JP 2010-090586.*

(Continued)

*Primary Examiner* — Monzer R Chorbaji
(74) *Attorney, Agent, or Firm* — Studebaker & Brackett PC

(57) ABSTRACT

A water discharge apparatus WD executes a water film formation step of ejecting running water and forming a water-splash suppression water film of the running water on a surface of a sterilization object, before executing a sterilization step of discharging sterilization water from a sterilization water ejection unit 20 toward the sterilization object.

6 Claims, 12 Drawing Sheets

(56) References Cited

OTHER PUBLICATIONS

International Search Report issued in PCT/JP2015/075549; dated Nov. 17, 2015.
International Preliminary Report on Patentability and Written Opinion issued in PCT/JP2015/075549; dated May 9, 2017.

* cited by examiner

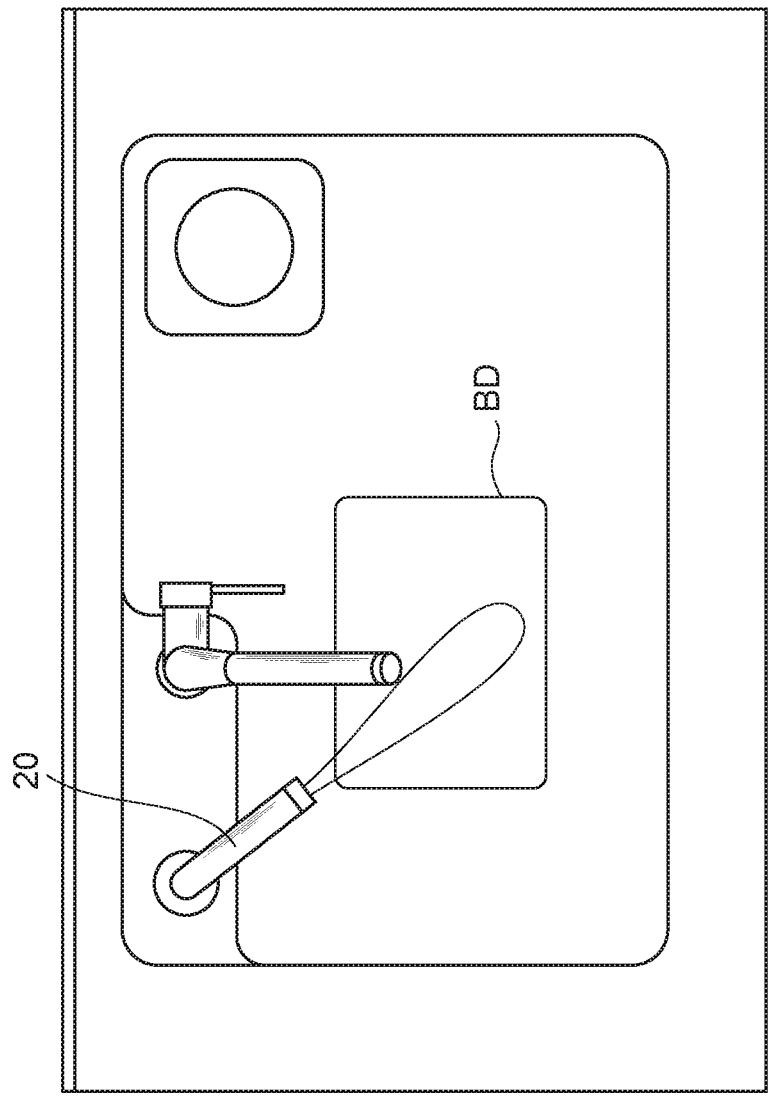

WATER DISCHARGE APPARATUS

TECHNICAL FIELD

The present invention relates to a water discharge apparatus that is provided in a kitchen.

BACKGROUND ART

In a water discharge apparatus that is provided in a kitchen, there is known a water discharge apparatus provided with a normal water faucet to eject a water flow in which the cross-sectional shape of the flux is a nearly circular shape, from a water discharge port, and a curtain-like water faucet to eject a curtain-like water flow from a water discharge port (see the following Patent Literature 1). The water discharge apparatus described in the following Patent Literature 1 is configured such that alkaline water generated by an ion water generator is ejected from the normal water faucet and acidic water generated by the ion water generator is ejected from the curtain-like water faucet.

CITATION LIST

Patent Literature

Patent Literature 1: Japanese Patent Laid-Open No. 10-82083

SUMMARY OF INVENTION

Technical Problem

In the meantime, for realizing a "concurrent sterilization" (a sterilization mode of sterilizing a chopping board or kitchen knife while performing cooking, to safely perform the next cooking work with the clean tool; the same applies hereinafter), it is desirable that the entire chopping board, for example, can be sterilized with a small amount of sterilization water for a short time. Here, focusing on the "concurrent sterilization" of the chopping board, for sterilizing the entire chopping board for a short time, it is important to secure a certain or higher rate as the water ejection rate of the sterilization water. Further, for sterilizing the entire chopping board with a small amount of sterilization water, it is important to hold most of the sterilization water having reached the chopping board once, on the chopping board, as long as possible.

However, when the certain rate is secured as the water ejection rate of the sterilization water, a water film to be formed when the sterilization water lands on the chopping board becomes large. Therefore, the sterilization water near the edge of the chopping board flows down from the chopping board, and thereby, most of the sterilization water flows down from the chopping board early. When most of the sterilization water flows down from the chopping board in this way, the entire chopping board cannot be sterilized with a small amount of sterilization water.

Hence, it is effective to discharge the sterilization water in a shower form or in a mist form. However, when the sterilization water is discharged in a shower form or in a mist form, a large water splash is prone to occur at the start of the discharge. This is because the discharge water in a shower form or the discharge water in a mist form has a high flow rate and is light so that a large water splash is prone to occur compared to rectified discharge water. The sterilization water has an oxidative power, causing a specific problem, in that metal products such as a water faucet around a sink is corroded when the splashed sterilization water adheres to the metal products for a long time.

The present invention has been made in view of the problem, and an object thereof is to provide a water discharge apparatus that can suppress the corrosion of metal products such as a water faucet even when the sterilization water is ejected in a shower form or in a mist form.

Solution to Problem

For solving the above problem, a water discharge apparatus according to the present invention is a water discharge apparatus that is provided in a kitchen, and includes: a sterilization water generation unit to generate sterilization water; a sterilization water ejection unit to eject the sterilization water generated by the sterilization water generation unit, in a shower form or in a mist form; a switching valve to switch between water discharge and water stop from the sterilization water ejection unit; and a control unit to control the sterilization water generation unit and the switching valve. When a water discharge start signal for the sterilization water is input, the control unit executes a water film formation step before executing a sterilization step, the sterilization step being a step of discharging the sterilization water from the sterilization water ejection unit toward a sterilization object, the water film formation step being a step of ejecting running water and forming a water-splash suppression water film of the running water on a surface of the sterilization object.

According to the present invention, since the sterilization water is ejected in a shower form or in a mist form, it is possible to reduce the water film that is formed at the time of landing on a chopping board, and it is possible to prevent most of the sterilization water from flowing down from the chopping board early. Thereby, it is possible to sterilize the entire chopping board with a small amount of sterilization water for a short time. Furthermore, since the water film formation step with the running water is executed before the sterilization step, the sterilization water in a shower form or in a mist form lands on the water film of the running water. Therefore, it is possible to suppress the water splash at the start of the discharge of the sterilization water. Thereby, even when the sterilization water is ejected in a shower form or in a mist form, it is possible to suppress the occurrence of the corrosion of metal products such as a water faucet around a sink due to the adhesion of the sterilization water.

For solving the above problem, a water discharge apparatus according to the present invention is a water discharge apparatus that is provided in a kitchen, and includes: a sterilization water generation unit to generate sterilization water; a sterilization water ejection unit to eject the sterilization water generated by the sterilization water generation unit, in a shower form or in a mist form; a switching valve to switch between water discharge and water stop from the sterilization water ejection unit; and a control unit to control the sterilization water generation unit and the switching valve. When a water discharge start signal for the sterilization water is input, the control unit executes a water film formation step before executing a sterilization step, the sterilization step being a step of discharging the sterilization water from the sterilization water ejection unit toward a sterilization object, the water film formation step being a step of ejecting sterilization water having a lower concentration than the sterilization water and forming a water-splash suppression water film of the sterilization water having the lower concentration on a surface of the sterilization object.

According to the present invention, since the sterilization water is ejected in a shower form or in a mist form, it is possible to reduce the water film that is formed at the time of landing on a chopping board, and it is possible to prevent most of the sterilization water from flowing down from the chopping board early. Thereby, it is possible to sterilize the entire chopping board with a small amount of sterilization water for a short time. Furthermore, since the water film formation step with the sterilization water having a low concentration is executed before the sterilization step, the sterilization water in a shower form or in a mist form lands on the water film of the sterilization water having a low concentration. Therefore, it is possible to suppress the water splash at the start of the discharge of the sterilization water having a relatively high concentration. Although the sterilization water having a low concentration is used in the water film formation step, there is less concern of the corrosion even when the sterilization water adheres to metal products such as a water faucet by water splash, because of a low concentration thereof. Further, since the sterilization water having a low concentration is used in the water film formation step, it is possible to lessen the concentration dilution of the sterilization water having a relatively high concentration. Thereby, even when the sterilization water having a relatively high concentration is discharged in a shower form or in a mist form, it is possible to suppress the occurrence of the corrosion of metal products such as a water faucet around a sink due to the adhesion of the sterilization water.

Further, in the water discharge apparatus according to the present invention, it is preferable that the control unit automatically perform switching from the water film formation step to the sterilization step, without waiting for an instruction that is input by a user.

In the preferable aspect, the user does not need to input the instruction for the switching from the water film formation step to the sterilization step. Therefore, the user can focus on a work for avoiding the water film on the chopping board from flowing down, and can make the sterilization water land on the chopping board while the water film formed on the chopping board is maintained.

Further, in the water discharge apparatus according to the present invention, it is preferable that the control unit perform the switching from the water film formation step to the sterilization step, without performing the water stop.

If a water stop step is performed between the water film formation step and the sterilization step, the time during the water stop step is a waiting time, and there is a fear that the water film flows down from the chopping board in the waiting time. In the preferable aspect, since the water stop step is not provided, it is possible to make the sterilization water land on the chopping board while the water film formed on the chopping board is maintained.

Further, in the water discharge apparatus according to the present invention, it is preferable that the water film formation step be executed by the water discharge from the sterilization water ejection unit.

If a water discharge part for forming the water film and a water discharge part for discharging the sterilization water are different in position, there is a fear that the water film unexpectedly flows down from the chopping board when the position of the water discharge is changed. In the preferable aspect, since the water film formation step is executed by the water discharge from the sterilization water ejection unit, the water discharge position is identical. The user can focus on a work for avoiding the water film on the chopping board from flowing down, and therefore, can make the sterilization water land on the chopping board while the water film formed on the chopping board is maintained.

Advantageous Effects of Invention

According to the present invention, it is possible to provide a water discharge apparatus that can suppress the corrosion of metal products such as a water faucet even when the sterilization water is ejected in a shower form or in a mist form.

BRIEF DESCRIPTION OF DRAWINGS

FIG. 11 is a diagram for describing the water discharge form of the water discharge apparatus according to the embodiment of the present invention.

DESCRIPTION OF EMBODIMENT

Figure 1:
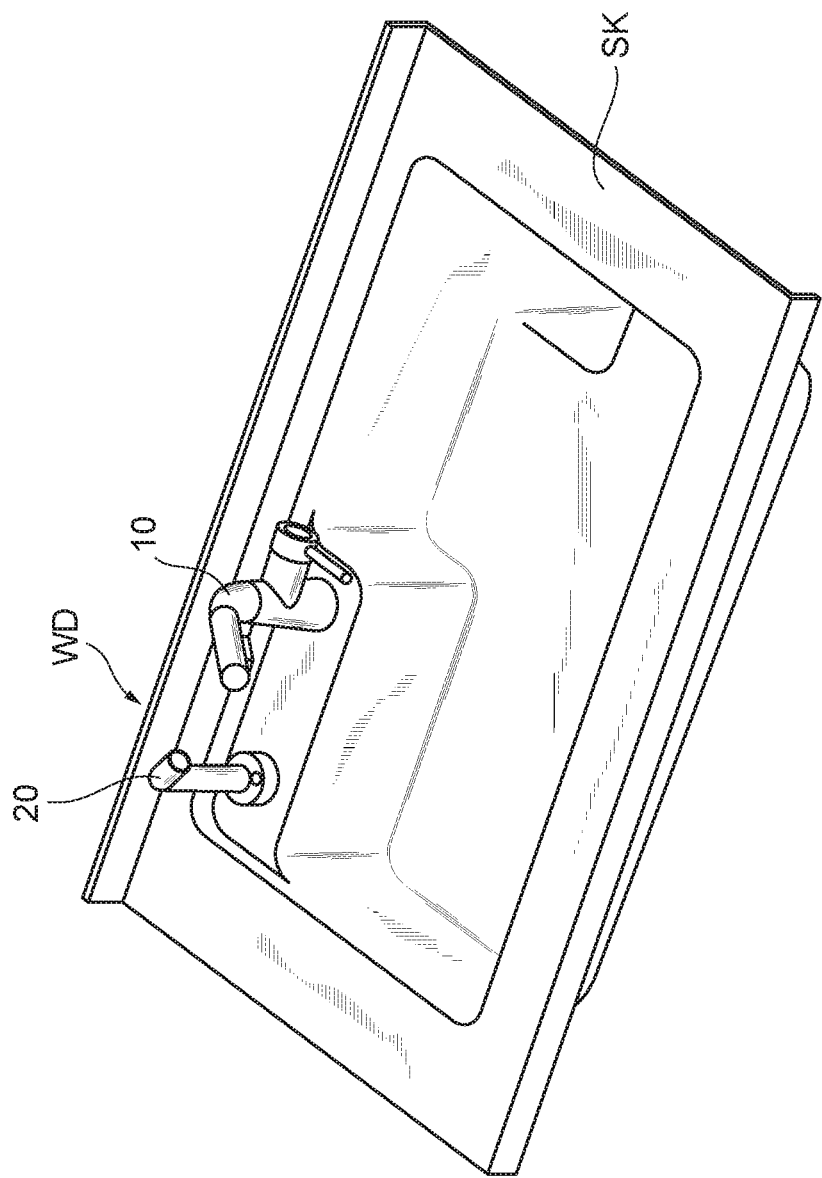
FIG. 1 is a perspective view showing the appearance of a water discharge apparatus according to an embodiment of the present invention.

Hereinafter, an embodiment of the present invention will be described with reference to the accompanying drawings. For facilitating the understanding of the description, in the drawings, identical reference characters are assigned to identical constituent elements as much as possible, and repetitive descriptions are omitted.

Figure 2:
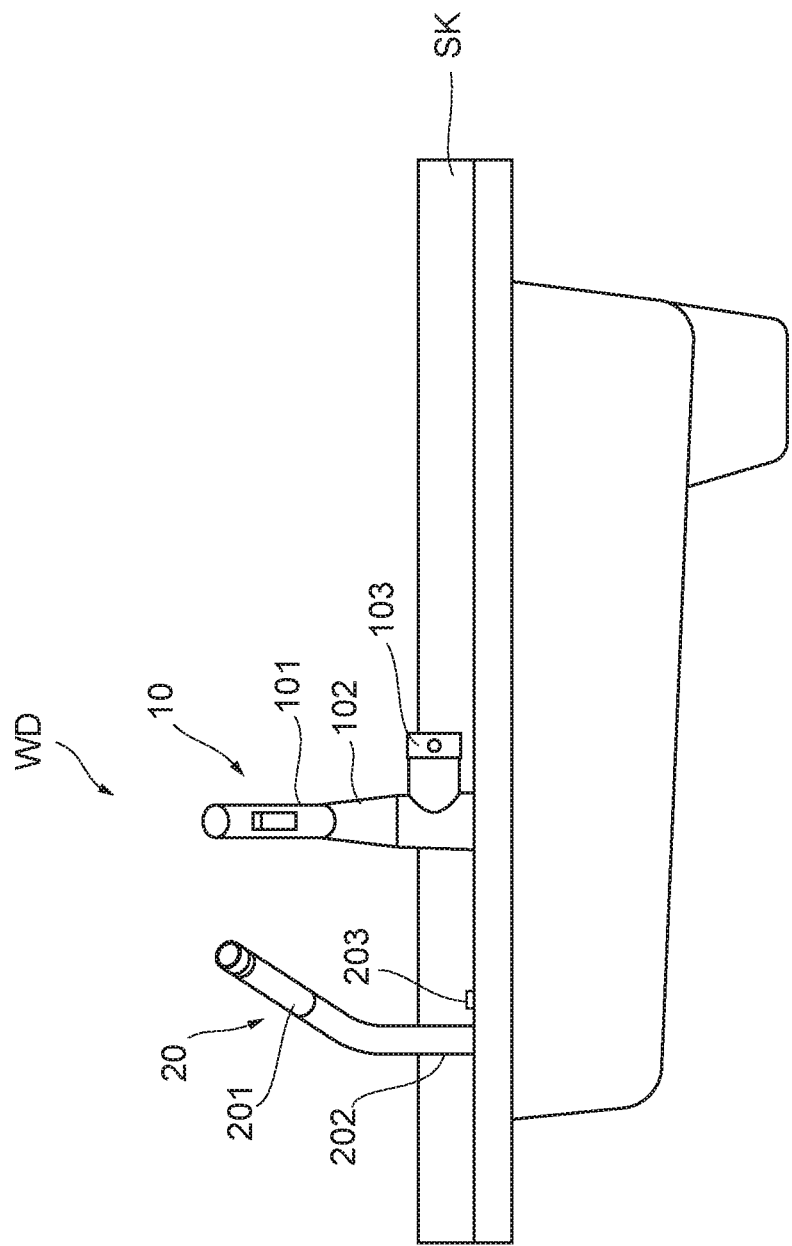
FIG. 2 is a front view showing the appearance of the water discharge apparatus according to the embodiment of the present invention.

A water discharge apparatus according to the embodiment of the present invention will be described with reference to FIG. 1 to FIG. 3. FIG. 1 is a perspective view showing the appearance of the water discharge apparatus according to the embodiment of the present invention. FIG. 2 is a front view showing the appearance of the water discharge apparatus according to the embodiment of the present invention. FIG.

3 is a plan view showing the appearance of the water discharge apparatus according to the embodiment of the present invention.

As shown in FIG. 1, a water discharge apparatus WD is provided in a sink SK. The water discharge apparatus WD includes a running water ejection unit 10 and a sterilization water ejection unit 20.

As shown in FIG. 2, the running water ejection unit 10 includes a spout unit 101, an attachment unit 102 and an operation unit 103. The sterilization water ejection unit 20 includes a spout unit 201, an attachment unit 202 and an operation unit 203.

Figure 3:
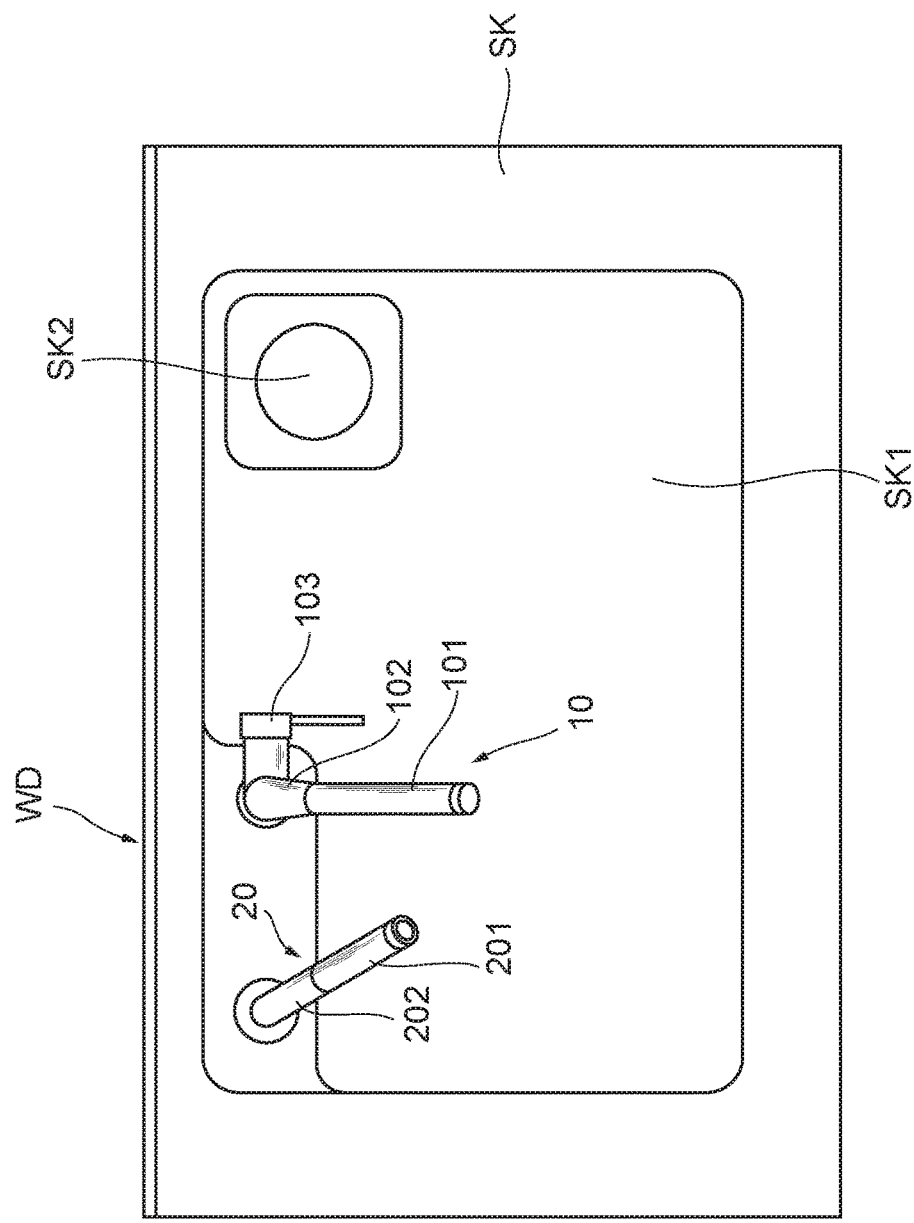
FIG. 3 is a plan view showing the appearance of the water discharge apparatus according to the embodiment of the present invention.

As shown in FIG. 3, the sink SK includes a bottom surface SK1 and a drainage port SK2. The drainage port SK2 is provided at one edge part in the width direction of the sink SK. The bottom surface SK1 has a drainage slope such that water flows toward the drainage port SK2. The sterilization water ejection unit 20 is disposed at the side opposite to the drainage port SK2, and is provided at the other edge part in the width direction of the sink SK. The running water ejection unit 10 is disposed near the central part.

Figure 4:
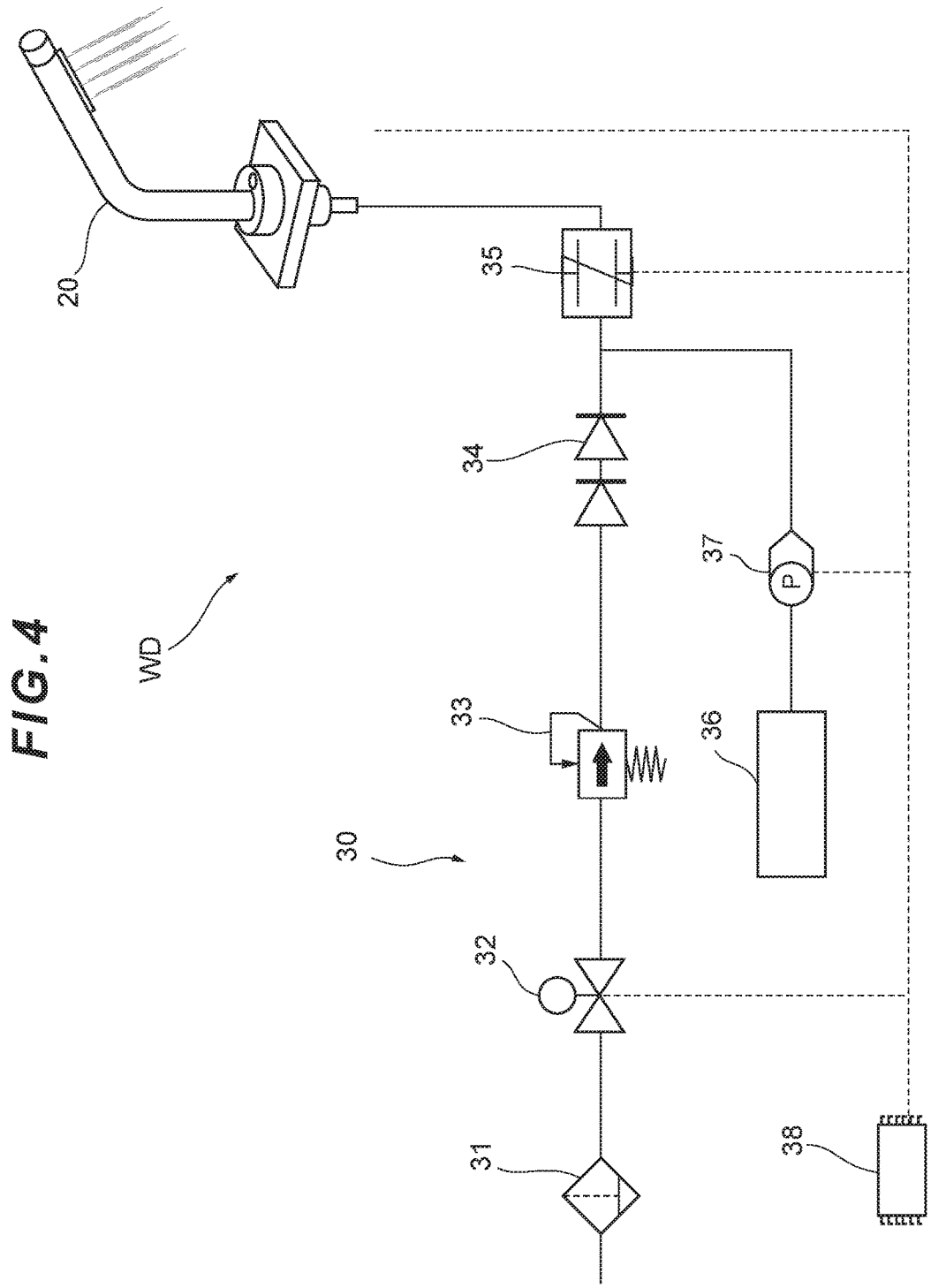
FIG. 4 is a schematic diagram showing a flow path configuration of the water discharge apparatus according to the embodiment of the present invention.

Next, a flow path configuration of the water discharge apparatus WD will be described with reference to FIG. 4. FIG. 4 shows a flow path configuration on the side of the sterilization water ejection unit 20 of the water discharge apparatus WD. As shown in FIG. 4, a sterilization water generation unit 30 is connected with the sterilization water ejection unit 20, and the sterilization water generation unit 30 supplies sterilization water.

The sterilization water generation unit 30 includes a stop cock 31, an electromagnetic valve 32, a pressure regulating valve 33, a check valve 34, an electrolysis tank 35, a salt water pack 36, a micro-pump 37 and a control device 38. A pipe pathway is connected with, from the upstream side, the stop cock 31, the electromagnetic valve 32, the pressure regulating valve 33, the check valve 34 and the electrolysis tank 35, and is connected with the sterilization water ejection unit 20, at the end. The salt water pack 36 and the micro-pump 37 are provided as a branch pathway, which is connected from the salt water 36 to the micro-pump and is connected to the above pipe pathway upstream of the electrolysis tank 35. The control device 38 outputs control signals to the electromagnetic valve 32, the electrolysis tank 35 and the micro-pump 37, respectively. The electromagnetic valve 32 opens/closes a valve so as to perform water discharge/water stop, in response to the control signal output from the control device 38. In the electrolysis tank 35, a pair of electrodes is provided, and the state of the energization of the pair of electrodes can be changed in response to the control signal output from the control device 38. When the pair of electrodes is energized, the sterilization water is generated in the electrolysis tank 35 and is supplied to the sterilization water ejection unit 20. The micro-pump 37 feeds the salt water stored in the salt water pack 36, to the electrolysis tank 35, in response to the control signal output from the control device 38. In this way, sterilization water having a high concentration is generated in the electrolysis tank 35.

Figure 5:
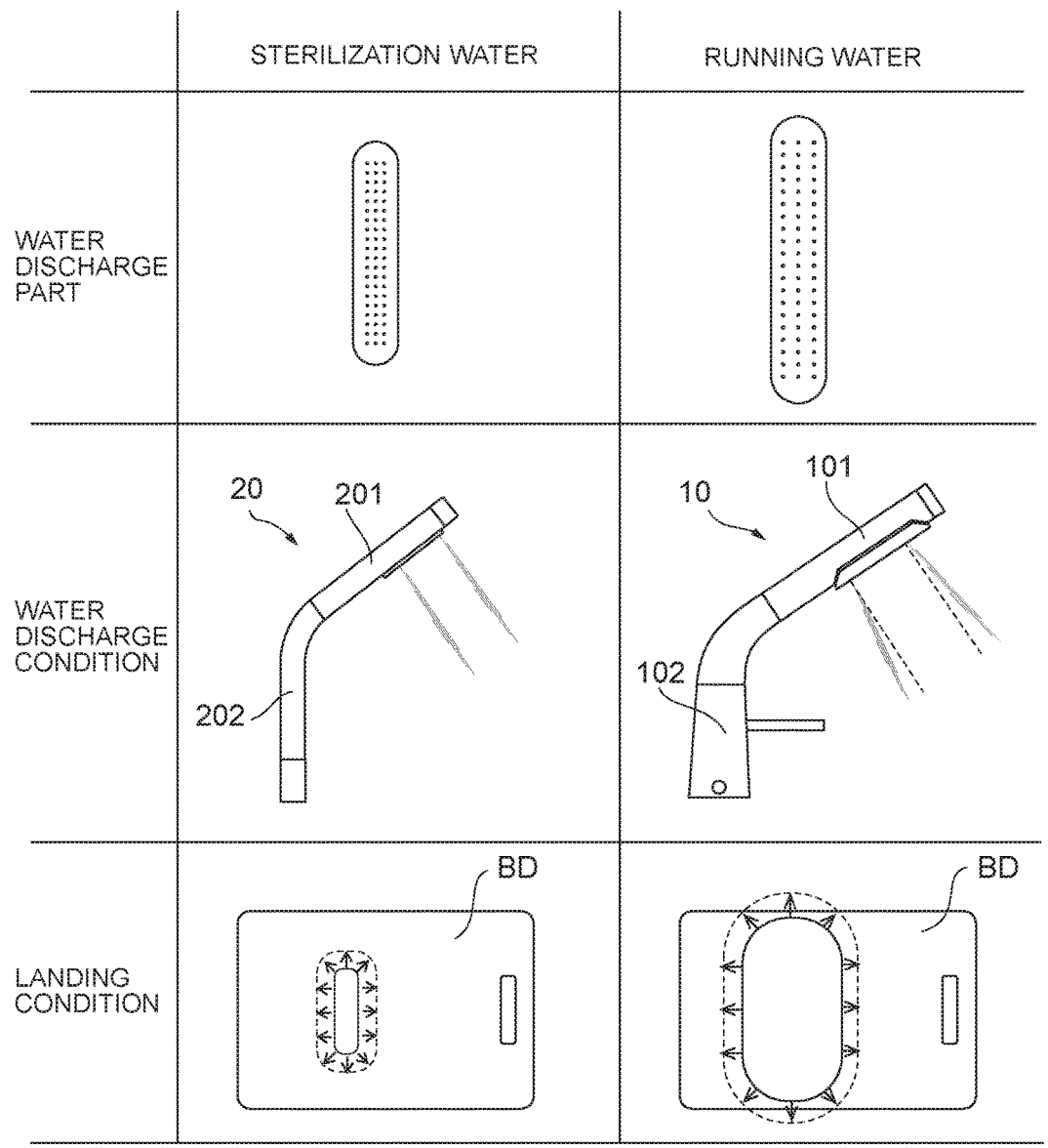
FIG. 5 is a diagram for describing water discharge forms of the water discharge apparatus according to the embodiment of the present invention.

Next, water discharge forms of the water discharge apparatus WD in the embodiment will be described with reference to FIG. 5. FIG. 5 shows the comparison between the water discharge condition of running water to be discharged from the running water ejection unit 10 and the water discharge condition of the sterilization water to be discharged from the sterilization water ejection unit 20.

In the comparison between a water discharge part formed on the spout unit 101 of the running water ejection unit 10 and the a water discharge part formed on the spout unit 201 of the sterilization water ejection unit 20, the outer circumference shape of the water discharge part formed on the spout unit 201 of the sterilization water ejection unit 20 is smaller. The water discharge part formed on the spout unit 201 of the sterilization water ejection unit 20 is formed so as to be smaller than the water discharge part formed on the spout unit 101 of the running water ejection unit 10 both in the width direction and in the depth direction. The outer circumference area of a region where a plurality of sterilization water sprinkling holes is formed is configured to be smaller than the outer circumference area of a region where a plurality of running water sprinkling holes is formed, such that the area of a water film to be formed at the time of the landing of the sterilization water ejected from the sterilization water ejection unit 20 is smaller than the area of a water film to be formed at the time of the landing of the running water ejected from the running water ejection unit 10. Furthermore, the interval between adjacent sterilization water sprinkling holes is configured to be smaller than the interval between adjacent running water sprinkling holes.

The condition of the water discharge from the water discharge part formed on the spout unit 101 of the running water ejection unit 10 is configured to start gradually spreading immediately after the water discharge. On the other hand, the condition of the water discharge from the water discharge part formed on the spout unit 201 of the sterilization water ejection unit 20 is configured not to spread as much as possible immediately after the water discharge. Therefore, as for the condition of the landing on a chopping board BD, the running water lands in a wide range and the sterilization water lands in a narrow range.

Figure 6:
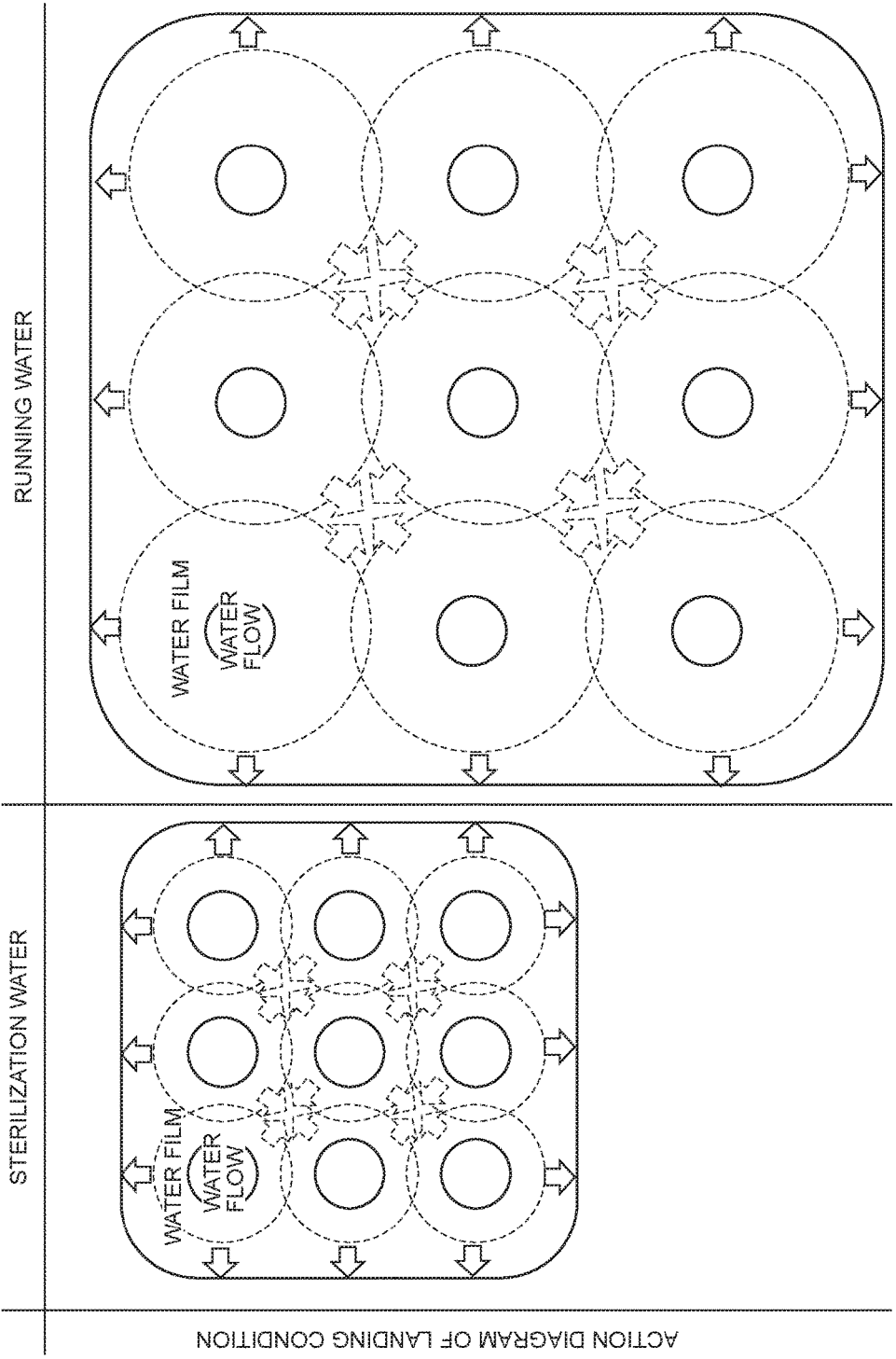
FIG. 6 is a diagram for describing actions of landing conditions in the water discharge forms described in FIG. 5.

When such water discharge conditions and landing conditions are realized, landing conditions shown in FIG. 6 are obtained by moving the chopping board BD after the landing. Thereby, as the landing condition of the sterilization water, water flows land in a narrow range and interfere with each other in the narrow range. Therefore, as a whole, the water spreads in a narrower range, compared to the landing condition of the running water. As a result, the sterilization water is smaller in the amount of the water that falls from the chopping board BD.

Figure 7:
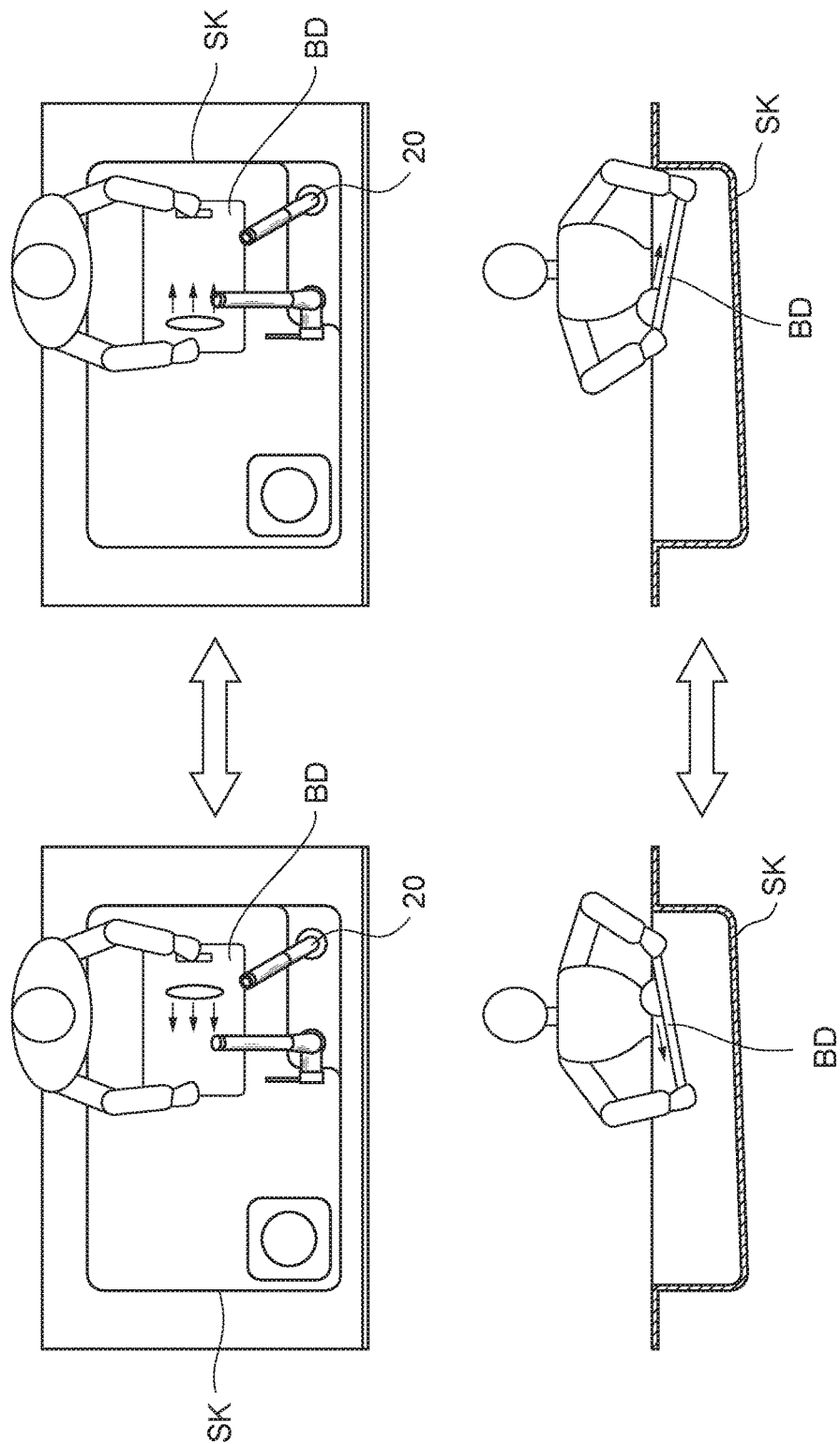
FIGS. 7A and 7B are diagrams for describing a work method for chopping board sterilization.

After the landing conditions shown in FIG. 6, by tilting the chopping board BD right and left as shown in FIGS. 7A and 7B, a user can distribute the sterilization water held on the chopping board BD, evenly over the chopping board BD.

Figure 8:
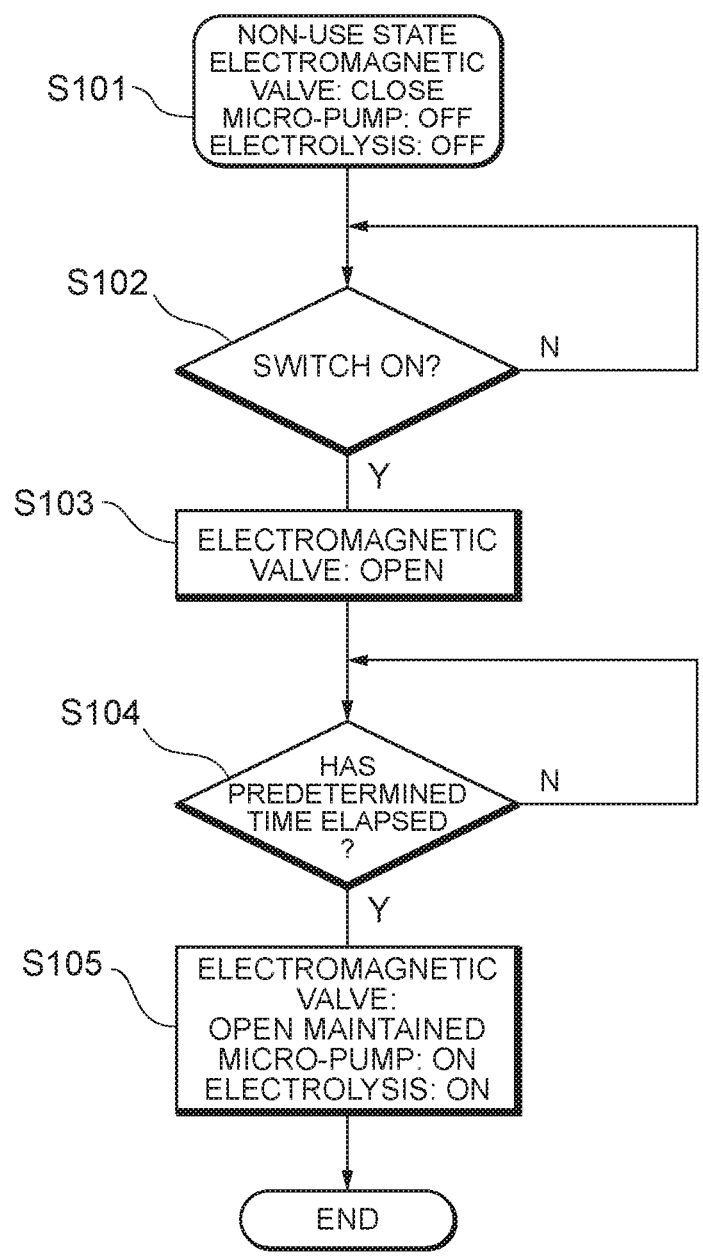
FIG. 8 is a flowchart of a control at the start of the water discharge in the water discharge apparatus according to the embodiment of the present invention.

Next, a flow of a control at the start of the water discharge on the sterilization water side of the water discharge apparatus WD will be described with reference to FIG. 8. At the start, a non-use state in which the electromagnetic valve 32 is closed, the micro-pump 37 is in the off-state and the electrolysis tank 35 is not energized is assumed (step S101).

The control device 38 judges whether the operation unit 203 has been operated and the ejection of the sterilization water has been requested (step S102). If the operation unit 203 has not been operated, the judgment in step S102 is repeated, and if the operation unit 203 has been operated, the flow proceeds to a process in step S103.

In step S103, the control device 38 outputs a control signal for opening the electromagnetic valve 32. In step S104 following step S103, whether a predetermined time has elapsed is judged. If the predetermined time has not elapsed, the judgment in step S104 is repeated, and if the predetermined time has elapsed, the flow proceeds to a process in step S105.

In step S105, the control device 38 maintains the open-state of the electromagnetic valve 32, drives the micro-pump 37, energizes the electrodes in the electrolysis tank 35, and generates the sterilization water having a high concentration. The sterilization water is ejected from the sterilization water ejection unit 20 toward the sink SK.

Figure 9C:
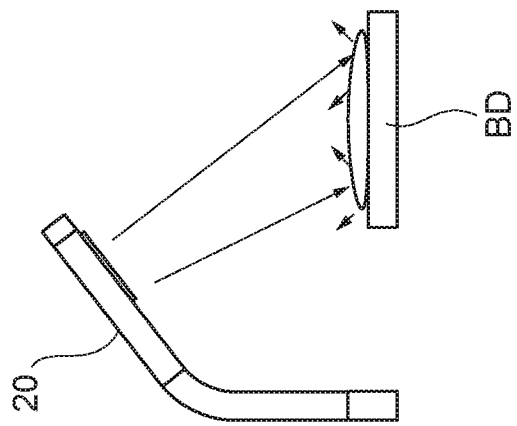
FIGS. 9A to 9C are diagrams for describing a situation in which a water film is formed by running water and water splash is suppressed.
Figure 9B:
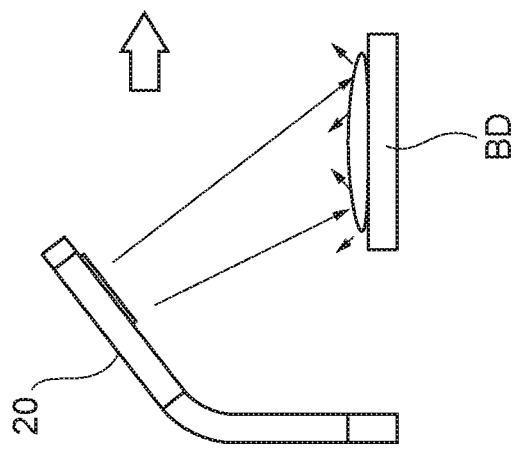
Figure 9A:
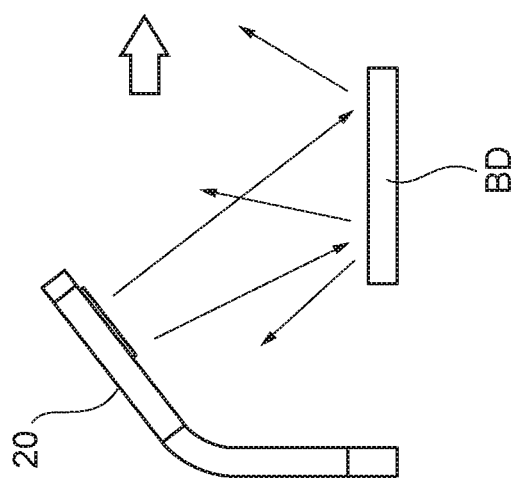

When the sterilization water is ejected in such steps, the running water is initially ejected to the chopping board BD, and thereafter the sterilization water is ejected. As shown in FIG. 9A, some of the running water initially having reached the chopping board BD remains on the chopping board BD, while the water splash occurs. Subsequently, as shown in FIG. 9B, the sterilization water reaches the chopping board BD. The water splash of the sterilization water is lessened because a water film of the running water has been already formed. Furthermore, as shown in FIG. 9C, also in a state where the water remaining on the chopping board BD is the sterilization water, the water splash of the subsequent sterilization water can be still lessened.

Figure 10:
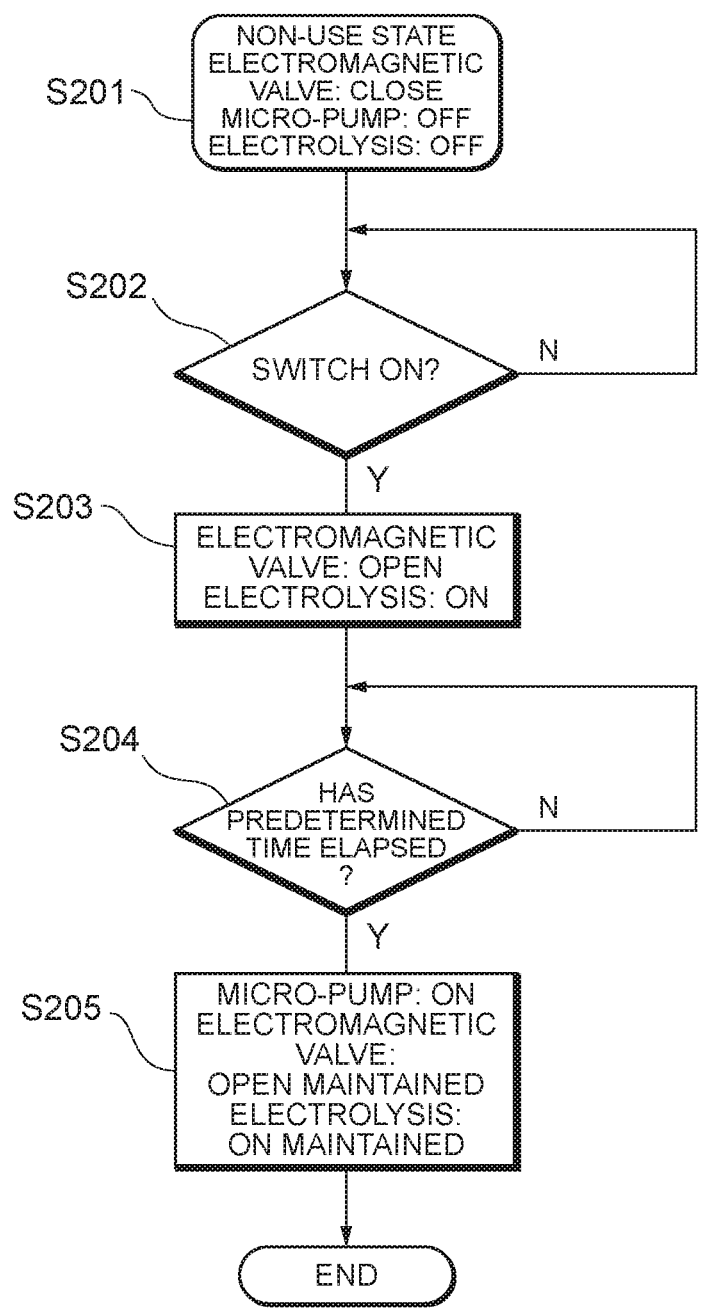
FIG. 10 is a flowchart of a control at the start of the water discharge in the water discharge apparatus according to the embodiment of the present invention.

Next, a flow of another control at the start of the water discharge on the sterilization water side of the water discharge apparatus WD will be described with reference to FIG. 10. At the start, the non-use state in which the electromagnetic valve 32 is closed, the micro-pump 37 is in the off-state and the electrolysis tank 35 is not energized is assumed (step S201).

The control device 38 judges whether the operation unit 203 has been operated and the ejection of the sterilization water has been requested (step S202). If the operation unit 203 has not been operated, the judgment in step S202 is repeated, and if the operation unit 203 has been operated, the flow proceeds to a process in step S203.

In step S203, the control device 38 outputs the control signal for opening the electromagnetic valve 32, and energizes the electrodes in the electrolysis tank 35. In step S204 following step S203, whether a predetermined time has elapsed is judged. If the predetermined time has not elapsed, the judgment in step S204 is repeated, and if the predetermined time has elapsed, the flow proceeds to a process in step S205.

In step S205, the control device 38 maintains the open-state of the electromagnetic valve 32, drives the micro-pump 37, maintains the energization of the electrodes in the electrolysis tank 35, and generates the sterilization water having a high concentration. The sterilization water is ejected from the sterilization water ejection unit 20 toward the sink SK.

Even when the sterilization water is ejected in such steps, sterilization water having a low concentration reaches the chopping board BD until the micro-pump 37 is driven, and therefore, a water film of the sterilization water having a low concentration is formed, allowing for the suppression of the water splash of the sterilization water having a high concentration.

In the embodiment, as shown in FIG. 11, the sterilization water ejection unit 20 is disposed at a position away from the center position in the right-left direction of the sink SK. Furthermore, the sterilization water ejection unit 20 ejects the sterilization water, toward the center side of the sink SK and in an oblique direction with respect to the front-back direction.

Figure 12A:
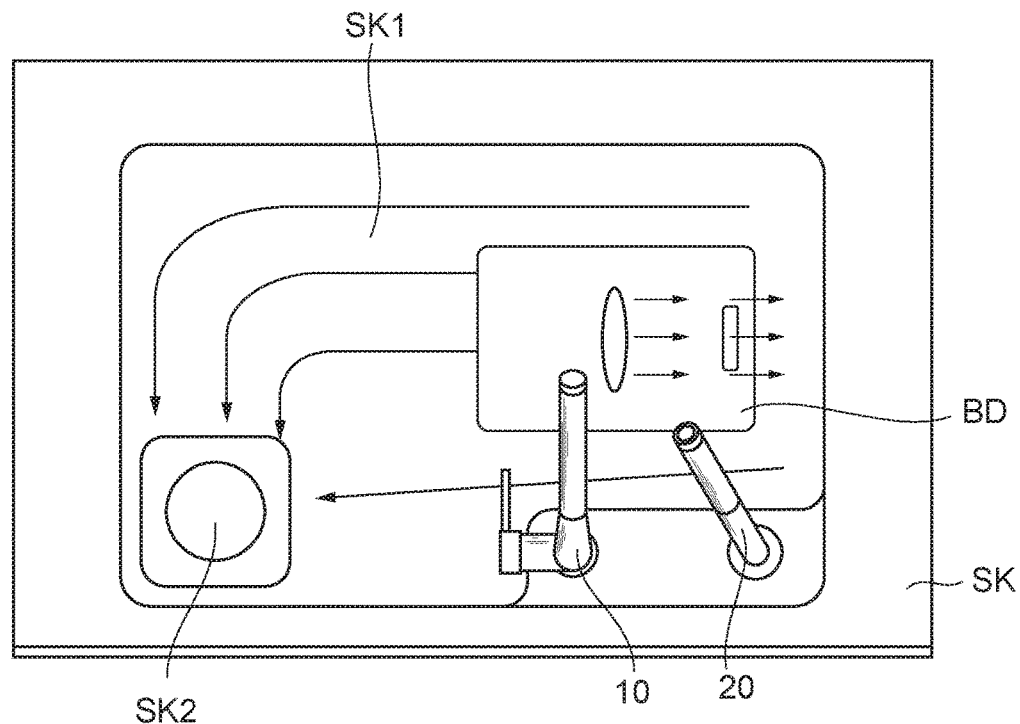
FIGS. 12A and 12B are diagrams for describing the water discharge form of the water discharge apparatus according to the embodiment of the present invention.
Figure 12B:
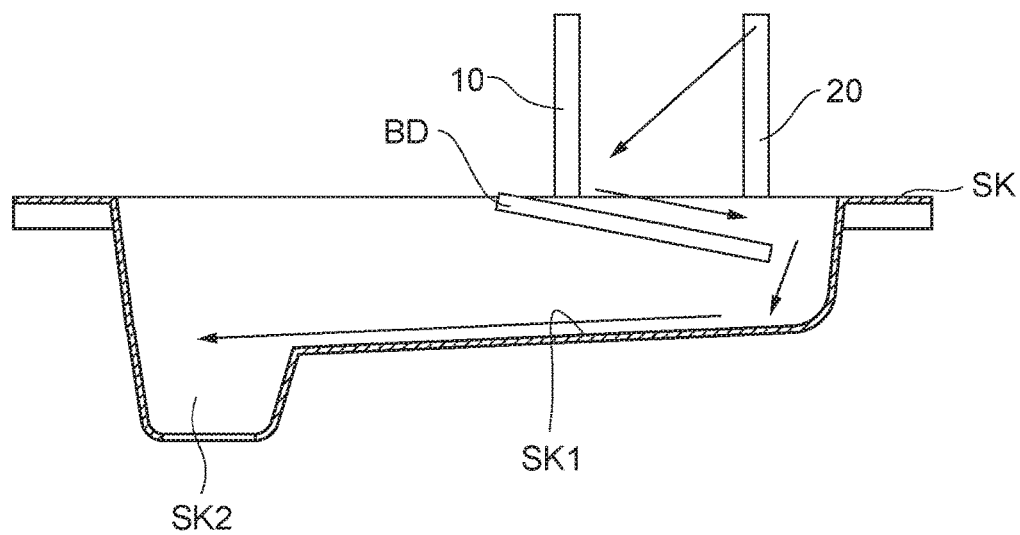

Further, as shown in FIGS. 12A and 12B, on the bottom surface SK1 of the sink SK, the drainage port SK2 is provided, and a slope surface part that is inclined downward toward the drainage port SK2 is formed. The drainage port SK2 is provided at one side in the right-left direction of the sink SK, and the sterilization water ejection unit 20 is provided at the other side in the right-left direction of the sink SK. The sterilization water ejection unit 20 is formed such that the outer circumference shape of the discharge water is a flat shape that is long in the front-back direction of the sink SK.

REFERENCE SIGNS LIST

10: running water ejection unit
20: sterilization water ejection unit
30: sterilization water generation unit
31: stop cock
32: electromagnetic valve
33: pressure regulating valve
34: check valve
35: electrolysis tank
36: salt water pack
37: micro-pump
38: control device
101: spout unit
102: attachment unit
103: operation unit
201: spout unit
202: attachment unit
203: operation unit
BD: chopping board
SK: sink
SK1: bottom surface
SK2: drainage port
WD: water discharge apparatus

The invention claimed is:

1. A water discharge apparatus that is provided in a kitchen, the water discharge apparatus comprising:
   a sterilization water generation unit to generate sterilization water;
   a sterilization water ejection unit to eject the sterilization water generated by the sterilization water generation unit, in a shower form or in a mist form;
   a switching valve to switch between water discharge and water stop from the sterilization water ejection unit; and
   a control unit to control the sterilization water generation unit and the switching valve,
   wherein when a water discharge start signal for the sterilization water is input, the control unit executes a water film formation step before executing a sterilization step, the sterilization step being a step of discharging the sterilization water from the sterilization water ejection unit toward a sterilization object, the water film formation step being a step of ejecting running water and forming a water-splash suppression water film of the running water on a surface of the sterilization object, and
   wherein the control unit automatically performs switching from the water film formation step to the sterilization step, without waiting for an instruction that is input by a user.

2. The water discharge apparatus according to claim 1, wherein the control unit performs the switching from the water film formation step to the sterilization step, without performing the water stop.

3. The water discharge apparatus according to claim 2, wherein the water film formation step is executed by the water discharge from the sterilization water ejection unit.

4. The water discharge apparatus according to claim 1, further comprising:
   a running water ejection unit comprising a plurality of running water sprinkling holes configured for discharging running water in a shower form or a mist form, the running water ejection unit being formed separately from the sterilization water ejection unit,
wherein an outer circumference area of a region where a plurality of sterilization water sprinkling holes is formed in the sterilization water ejection unit is configured to be smaller than an outer circumference area of a region where the plurality of running water sprinkling holes is formed in the running water ejection unit, such that an area of a water film to be formed at the time of the landing of the sterilization water ejected from the sterilization water ejection unit is smaller than an area of a water film to be formed at the time of the landing of the running water ejected from the running water ejection unit.

5. The water discharge apparatus according to claim 4, wherein an interval between adjacent sterilization water sprinkling holes is smaller than an interval between adjacent running water sprinkling holes.

6. A water discharge apparatus that is provided in a kitchen, the water discharge apparatus comprising:
　a sterilization water generation unit to generate sterilization water;
　a sterilization water ejection unit to eject the sterilization water generated by the sterilization water generation unit, in a shower form or in a mist form;
　a switching valve to switch between water discharge and water stop from the sterilization water ejection unit; and
　a control unit to control the sterilization water generation unit and the switching valve,
wherein when a water discharge start signal for the sterilization water is input, the control unit executes a water film formation step before executing a sterilization step, the sterilization step being a step of discharging the sterilization water from the sterilization water ejection unit toward a sterilization object, the water film formation step being a step of ejecting sterilization water having a lower concentration of an ingredient having a sterilization effect than the sterilization water and forming a water-splash suppression water film of the sterilization water having the lower concentration of the ingredient having the sterilization effect on a surface of the sterilization object, and
wherein the control unit automatically performs switching from the water film formation step to the sterilization step, without waiting for an instruction that is input by a user.

\* \* \* \* \*